US00PP25870P3

(12) United States Plant Patent
Jury

(10) Patent No.: US PP25,870 P3
(45) Date of Patent: Sep. 8, 2015

(54) ***MICHELIA* PLANT NAMED 'MICJUR05'**

(50) Latin Name: *Michelia yunnanensis×doltsopa*
Varietal Denomination: MICJUR05

(71) Applicant: Mark Jury, Waitara (NZ)

(72) Inventor: Mark Jury, Waitara (NZ)

( * ) Notice: Subject to any disclaimer, the term of this patent is extended or adjusted under 35 U.S.C. 154(b) by 110 days.

(21) Appl. No.: 13/998,395

(22) Filed: Oct. 28, 2013

(65) Prior Publication Data

US 2015/0121581 P1 Apr. 30, 2015

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Susan McCormick Ewoldt
(74) *Attorney, Agent, or Firm* — Cassandra Bright

(57) ABSTRACT

A new and distinct *Michelia* cultivar named 'MICJUR05' is disclosed, characterized by having a pyramidal, moderately compact growth habit and abundant, fragrant, clear white flowers. Plants begin flowering in late Winter, and continue flowering for 12 weeks. The new variety is a *Michelia*, normally produced as a small ornamental tree or shrub.

2 Drawing Sheets

Figure 1:
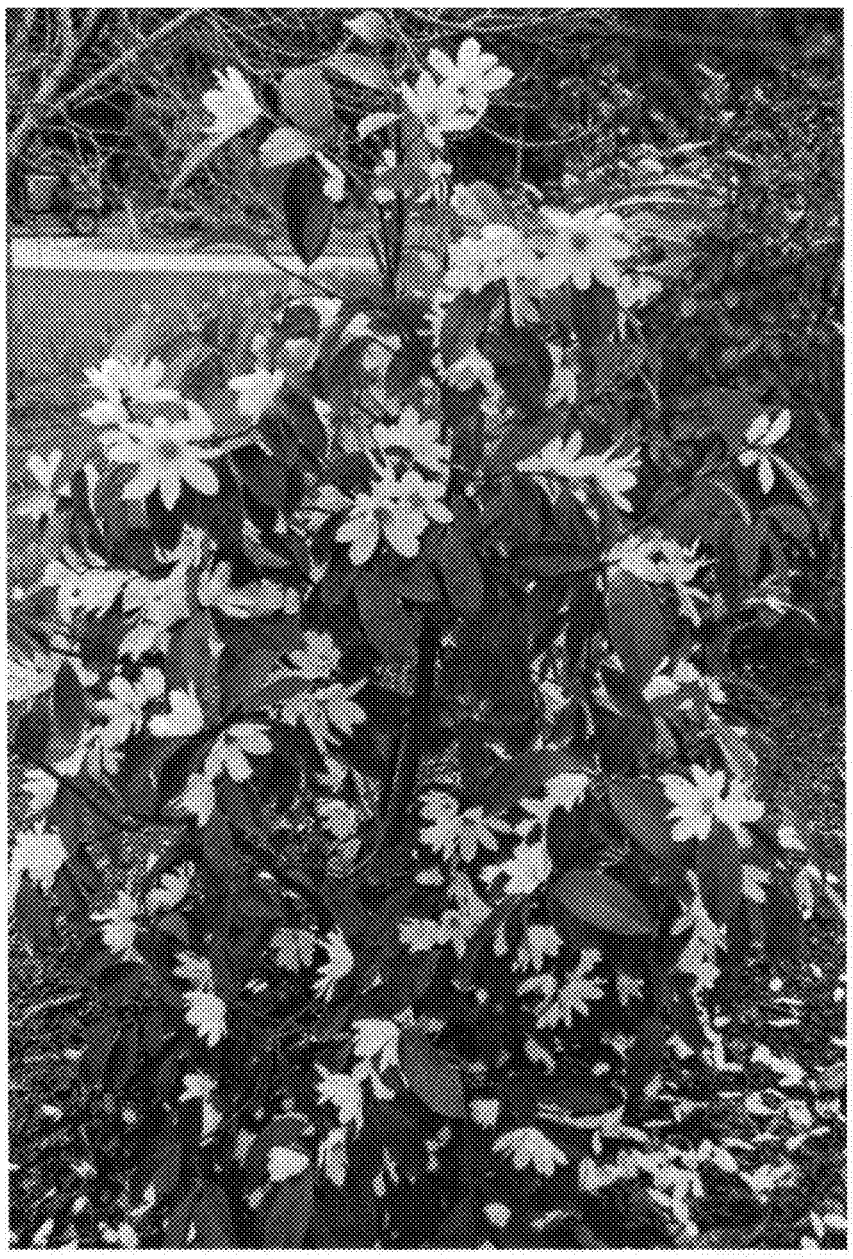

Latin name of the genus and species: *Michelia yunnanensis×doltsopa.*

Variety denomination: 'MICJUR05'.

BACKGROUND OF THE INVENTION

The new cultivar is a product of a planned breeding program. The new variety resulted from a crossing performed in 1995 in North Taranaki, Nth Is, New Zealand. The seed parent is the unpatented variety, *Michelia yunnanensis* 'Velvet and Cream'. The pollen parent is the unpatented variety *Michelia doltsopa* 'Silver Cloud'. The new variety was first selected in 1999, by the inventor, Mark Jury at a commercial nursery in North Taranaki, New Zealand.

Asexual reproduction of the new cultivar 'MICJUR05' by vegetative cuttings was first in performed in 2004 at a commercial nursery in New Zealand and has shown that the unique features of this cultivar are stable and reproduced true to type on successive generations.

SUMMARY OF THE INVENTION

The cultivar 'MICJUR05' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'MICJUR05'. These characteristics in combination distinguish 'MICJUR05' as a new and distinct *Michelia* cultivar:

1. Medium sized evergreen shrub or tree.
2. Late Winter/Early Spring flowering
3. Pyramidal growth habit.
4. Moderately dense growth.
5. Clear white flowers.
6. Strong fragrance to flowers.
7. Usefulness as a street tree, hedge, topiary or specimen tree.

8. Bronze underside to foliage
8. Long flowering season.
9. Large quantity of flowers.
10. Good lastingness of flowers

PARENT COMPARISON

Plants of the new cultivar 'MICJUR05' are similar to plants of the seed parent, *Michelia yunnanensis* 'Velvet and Cream' in most horticultural characteristics, however, plants of the new cultivar 'MICJUR05' have larger flowers and larger foliage. Additionally, plants of the new variety produce flowers with more fragrance than those of the seed parent.

Plants of the new cultivar 'MICJUR05' are similar to plants of the pollen parent, *Michelia doltsopa* 'Silver Cloud' in most horticultural characteristics. However, plants of the new cultivar are much shorter overall, and have a more controlled growth habit. Additionally, the new variety has a different floral scent. 'MICJUR05' can be grown from cuttings, whereas 'Silver Cloud' requires grafting or budding.

COMMERCIAL COMPARISON

Plants of the new cultivar 'MICJUR05' are similar to plants of the pollen parent, *Michelia* hybrid 'MICJUR02', U.S. Plant patent application Ser. No. 13/987,703 in most horticultural characteristics. However, plants of the new cultivar differ in the following characteristics:

1. 'MICJUR05' has larger flowers.
2. 'MICJUR05' has larger foliage.
3. 'MICJUR05' begins flowering earlier in the season.
4. 'MICJUR05' has less glossy foliage.

BRIEF DESCRIPTION OF THE PHOTOGRAPH

The accompanying photograph in FIG. 1 illustrates in full color a typical plant of 'MICJUR05' grown outdoors. Age of the plant photographed is approximately 5 years from a rooted cutting.

Figure 2:
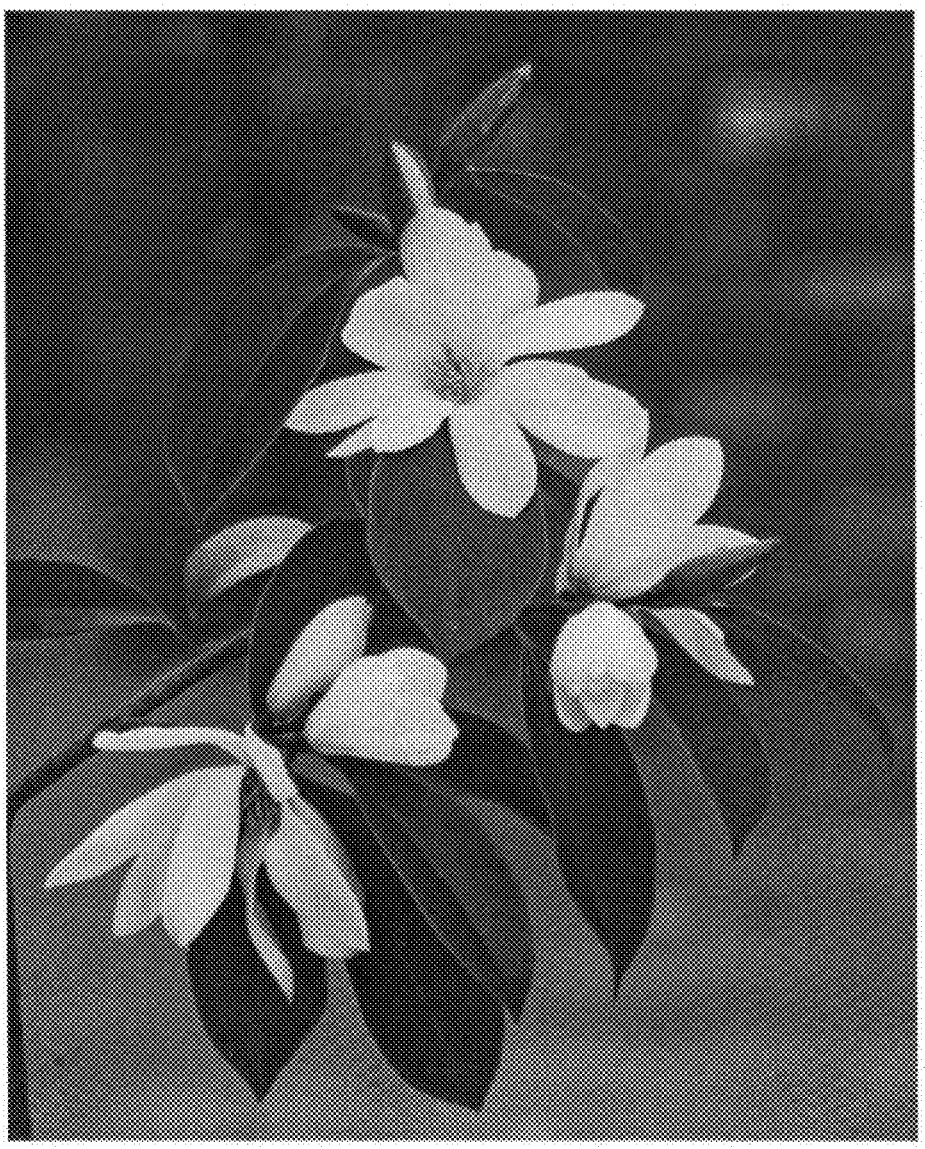

FIG. 2 illustrates in full color typical flowers of 'MICJUR05'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'MICJUR05' plants grown outdoors in New Zealand. Growing conditions are similar to USDA Zone 7. Age of the plants when described is approximately 4 years old. Measurements and numerical values represent averages of typical plant types.

Botanical classification: *Michelia yunnanensis*×*doltsopa* 'MICJUR05'.

PROPAGATION

Time to initiate roots: About 60 days at approximately 21° C.

Time to produce a rooted cutting: About 120 days at 21° C.

Root description: Typical *Michelia* root, thick, coarse, colored near RHS White 155A.

PLANT

Growth habit: Pyramidal shaped medium sized evergreen shrub or tree.

In a container or in the ground: Ground.

Height: Approximately 4 meters after 12 years.

Plant spread: Approximately 3.8 meters after 12 years.

Stem diameter: Approximately 20 cm after 12 years.

Branching characteristics: Depends upon cultural techniques. Without pruning, a single trunk tree with lateral branches form at acute angles to the trunk. With pruning, plants can be grown as large shrubs.

Individual branch characteristics (of 1 year old tree):

*Length*.—Up to 25 cm.

*Diameter*.—Up to 0.5 cm.

*Texture*.—Smooth.

*Color*.—Near RHS 197B.

Trunk:

*Diameter*.—Approximately 20 cm, after 12 years. Measured approximately 10 cm above the ground.

*Texture*.—Smooth.

*Color*.—Near RHS 197B.

FOLIAGE

Leaf:

*Arrangement*.—Mixed alternate, and occasionally opposite.

*Average length*.—Approximately 13.0 to 15.0 cm.

*Average width*.—Approximately 6.5 to 7.0 cm.

*Shape of blade*.—Elliptic.

*Apex*.—Acute to acuminate.

*Base*.—Rounded.

*Margin*.—Entire.

*Texture of top surface*.—Smooth, with glossy appearance.

*Texture of lower surface*.—Smooth.

*Leaf internode length*.—Approximately 3 cm.

*Color*.—Mature foliage upper side: Near RHS Yellow-Green 147A. Mature foliage under side: Near RHS Yellow-Green 146B.

Foliage:

*Venation*.—Type: Pinnate. Venation color upper side: Near RHS Yellow-Green 144C. Venation color under side: Near RHS Yellow-Green 144B.

*Petiole*.—Not present, sessile.

FLOWER

Natural flowering season: Flowering begins late Winter to early Spring. Lasts approximately 12 weeks.

Begins flowering after how many years/months: 1.5 to 2 years after planting an unrooted cutting.

Inflorescence type and habit: Solitary occurring, rotate. Flowers have a flattened concave aspect in the upper profile, and flattened convex aspect in the lower profile.

Quantity of flowers: Profuse, approximately 1500 per tree or shrub.

Individual flower size:

*Diameter*.—Approximately 13.0 to 14.0 cm.

*Depth*.—Approximately 6 cm.

Peduncle:

*Length*.—0.6 to 1.0 cm.

*Diameter*.—0.5 cm.

*Color*.—Near RHS Greyed-Orange 167A.

*Texture*.—Soft velvety pubescence.

Pedicel: Not present.

Petals:

*Petal arrangement*.—9 to 13 whorled, overlapping.

*Shape*.—Elliptic.

*Size*.—Length: 7.0 to 8.0 cm. Width: 2.5 to 3.5 cm.

*Margin*.—Entire.

*Apex*.—Acute.

*Base*.—Rounded.

*Petal quantity*.—Approximately 9 to 13.

*Texture*.—Smooth, all surfaces.

*Color*.—Petals: When opening: Upper surface: Near RHS White Ni 55D, basal spot Orange-White 159A. Lower surface: Near RHS White N155D. Fully opened: Upper surface: Near RHS White N155D, basal spot Orange-White 159A. Lower surface: Near RHS White N155D. Color Changes when aging: Upper surface: Near RHS White N155D, base Yellow-Green 154C. Lower surface: Near RHS White N155D.

Bud:

*Shape*.—Ovate to linear.

*Length*.—Approximately 2 cm.

*Diameter*.—Approximately 1 cm.

*Color*.—Near RHS Greyed-Orange 166B.

Sepals/tepals: Not Present.

Fragrance: Noticeable, pleasant fragrance.

REPRODUCTION ORGANS

Stamens:

*Number*.—Approximately 23.

*Filament length*.—Approximately 1.5 cm.

*Filament color*.—Near RHS Orange-White 159A.

Anthers:

*Length*.—Approximately 0.2 cm.

*Shape*.—Linear.

*Color*.—Near RHS Orange-White 159A.

Pistil:

*Number*.—1.

*Length*.—Approximately 2 cm.

*Style*.—Length: Approximately 1.8 cm. Color: Near RHS Yellow-Green 144A when immature. Matures to Greyed-Orange 166B.

*Pollen*.—Quantity: Moderate. Color: Near RHS Greyed-Orange 163B.

OTHER CHARACTERISTICS

Seeds and fruits: The new cultivar sets a small amount of seed irregularly.

*Fruit color*.—Begins near RHS Green Yellow-Green 144C, changes to Brown 200B before dropping off before mature.

*Seed size*.—Approximately 0.7 cm long, 0.2 cm wide. Colored Browtn 200B.

Disease/pest resistance: Neither resistance nor susceptibility to pathogens and pests common to *Michelia* have been observed.

Temperature tolerance: The new variety is suitable for growing in USDA zones 7b through 11.

What is claimed is:

1. A new and distinct cultivar of *Michelia* plant named 'MICJUR05' as herein illustrated and described.

* * * * *